US00PP22643P3

(12) United States Plant Patent
ten Have

(10) Patent No.: US PP22,643 P3
(45) Date of Patent: Apr. 10, 2012

(54) ***BEGONIA* PLANT NAMED 'HV01B1'**

(50) Latin Name: *Begonia elatior*
Varietal Denomination: HV01B1

(75) Inventor: Jos ten Have, Maasland (NL)

(73) Assignee: J&P Ten Haue B.V.

( * ) Notice: Subject to any disclaimer, the term of this patent is extended or adjusted under 35 U.S.C. 154(b) by 0 days.

(21) Appl. No.: 12/799,989

(22) Filed: May 5, 2010

(65) Prior Publication Data

US 2011/0277200 P1 Nov. 10, 2011

(51) Int. Cl.
*A01H 5/00* (2006.01)

(52) U.S. Cl. ..... Plt./344

(58) Field of Classification Search ..... Plt./344, Plt./346, 347
See application file for complete search history.

*Primary Examiner* — June Hwu
(74) *Attorney, Agent, or Firm* — Cassandra Bright

(57) ABSTRACT

A new and distinct *Begonia* cultivar named 'HV01B1' is disclosed, characterized by its bright green foliage with a notched margin and bright yellow/orange and red flowers. The new cultivar is a *Begonia,* typically suited for ornamental container use.

1 Drawing Sheet

Figure 1:
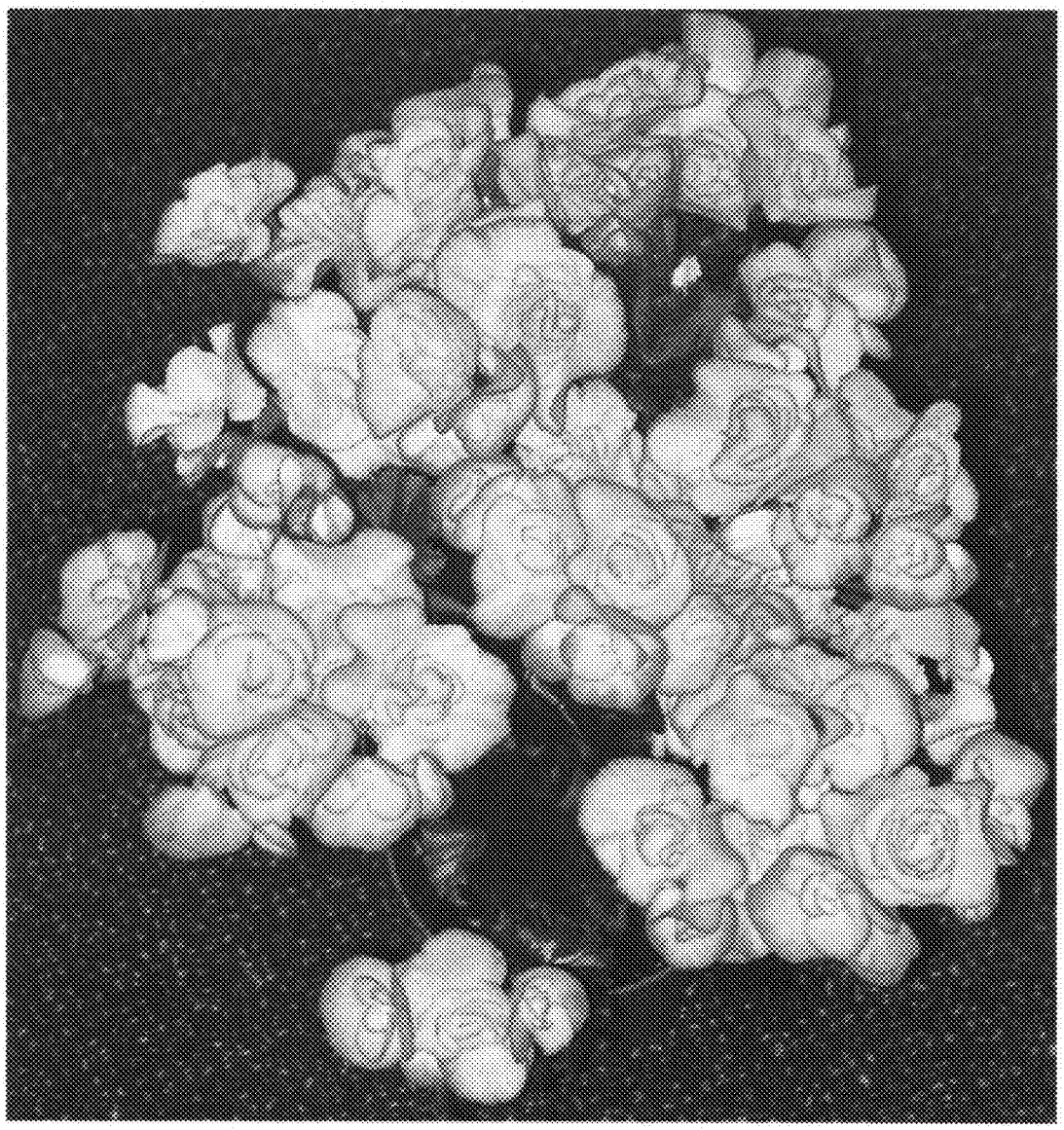

Latin name of the genus and species: *Begonia elatior.*
Variety denomination: 'HV01B1'.

BACKGROUND OF THE INVENTION

The new cultivar is the result of a chance discovery in an existing population of *Begonia elatior* plants. The new variety originated as a naturally occurring, whole plant mutation of the parent variety, the unpatented commercial variety, *Begonia elatior* 'Carnaval.' The new variety was discovered by the inventor, Jos ten Have, a citizen of the Netherlands, in the Summer of 2004 at a commercial greenhouse in Maasland, the Netherlands.

After selecting and isolating the new cultivar, asexual reproduction of the new cultivar 'HV01B1'was first performed in the same commercial greenhouse by vegetative cuttings in the winter of 2004. 'HV01B1' has since produced several generations and has shown that the unique features of this cultivar are stable and reproduced true to type.

SUMMARY OF THE INVENTION

The cultivar 'HV01B1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HV01B1'. These characteristics in combination distinguish 'HV01B1' as a new and distinct *Begonia* cultivar:

1. Bright green foliage.
2. Distinctively notched foliage margins.
3. Distinctive orange-yellow flowers with red margin.
4. Folded, ligulate floret.

PARENTAL COMPARISON

Plants of the new cultivar 'HV01B1' are similar to the parent 'Carnaval' in most horticultural characteristics. However, 'HV01B1' differs in producing foliage with a notched margin not found on 'Carnaval.' Additionally, 'HV01B1' produces a larger flowers, of a different shape and brighter color than 'Carnaval.'

COMMERCIAL COMPARISON

Plants of the new cultivar 'HV01B1' are best compared to the parent variety.

BRIEF DESCRIPTION OF THE PHOTOGRAPH

The accompanying photograph in FIG. 1 illustrates in full color a typical plant of 'HV01B1' grown in a greenhouse in Maasland, the Netherlands. This plant is approximately 10 weeks old, shown in a 10 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'HV01B1' plants grown in a greenhouse in Maasland, the Netherlands during the Fall months. Temperatures ranged from 18° C. to 20° C. at night to 19° C. to 20° C. during the day. No artificial light, photoperiodic treatments or chemical treatments were given to the plants. Measurements and numerical values represent averages of typical plant types.
Botanical classification: *Begonia elatior* 'HV01B1'.
Age of the plant described: Approximately 10 weeks.
Container size of the plant described: 10 cm commercial container.

PROPAGATION

Time to initiate roots:
*Summer.*—30 to 35 days at approximately 22° C.
*Winter.*—35 to 40 days at approximately 22° C.

Root description: Fine, densely branched, non-fibrous, non-fleshy, colored near Grey-Brown N199C.

PLANT

Growth habit: Broad upright.
Pot size of plant described: 17 cm.
Height: 25.3 cm.
Plant spread: 23.0 cm.
Growth rate: Moderate.
Branching characteristics: Free branching, from base as well as lateral branches.
Length of primary lateral branches: 13.4 cm.
Quantity of primary lateral branches: Average: 3.
Characteristics of primary lateral branches:
*Form.*—Rounded to elliptic.
*Diameter.*—Average: 1.0 cm.
*Color.*—RHS Yellow-Green 146B, with stripes near Yellow-Green 144B.
*Texture.*—Slightly glossy, sparsely covered with soft thin hairs, average length 2 mm, colored Near Green-White 157D, base strongly tinged Greyed-Orange 178B.
*Strength.*—Weak to moderately strong.
Internode length: 3.0 cm.

FOLIAGE

Leaf:
*Arrangement.*—Alternate.
*Quantity.*—Approximately 5 per branch.
*Average length.*—13.8 cm.
*Average width.*—10.9 cm.
*Shape of blade.*—Ovate to cordate.
*Apex.*—Acute.
*Base.*—Hastate, slightly overlapping.
*Margin.*—Denticulate, conspicuously wavy.
*Texture of top surface.*—Smooth, very glossy.
*Texture of bottom surface.*—Smooth.
*Pubescence.*—No leaf pubescence.
*Aspect.*—Leaves horizontally placed to slightly pointed downward.
*Color.*—Young foliage upper side: RHS Yellow-Green 152A, flushed along veins 144B. Young foliage under side: Range between Greyed-Orange 173B to 174B, flushed along veins Yellow-Green 144B. Mature foliage upper side: Near RHS Green 137A but much darker. Mature foliage under side: RHS Yellow-Green 148B.
*Venation.*—Type: Pinnate. Venation color upper side: RHS Yellow-Green 146C. Venation color under side: RHS Yellow-Green 146C.
*Petiole.*—Length: 6.2 cm. Diameter: 0.6 cm. Color: Near RHS Yellow-Green 152C, basal end. Distal end near RHS Greyed-Red 180A and 180B.
*Texture.*—Slightly glossy, sparsely covered with soft thin hairs, average length 2 mm, colored near Green-White 157D.
*Stipule description.*—Length: 1.8 cm. Diameter: 1.5 cm. Color: Near RHS Yellow-Green 144C, margins darker; 144B. Texture: Smooth, slightly glossy.

FLOWER

Natural flowering season: Early spring through late summer.
Days to flowering from rooted cutting: 8-10 weeks.
Inflorescence and flower type and habit: Axillary and terminal clusters; individual flowers fully double. Only one type of sterile flowers present.
Rate of flower opening: 5 to 10 days from bud to fully opened flower.
Flower longevity on plant: Average: 28 days.
Persistent or self-cleaning: Self-cleaning.
Bud:
*Shape.*—Inverted triangular.
*Length.*—2.2 cm.
*Diameter.*—3.1 cm.
*Color.*—Near RHS Yellow-Green 145C, top margin near RHS Red 41A and 41B.
Inflorescence size:
*Diameter.*—Approximately 18 cm.
*Depth.*—Approximately 5 cm.
Flower size:
*Diameter.*—6.2 cm.
*Depth.*—2.6 cm.
Flower bracts:
*Quantity.*—2.
*Arrangement.*—Opposite.
*Length.*—4.0 cm.
*Width.*—5.4 cm.
*Shape.*—Reniform.
*Apex.*—Rounded.
*Base.*—Truncate to reniform.
*Margin.*—Entire.
*Texture, upper and lower surfaces.*—Smooth, lower surface very slightly glossy, upper side dull.
*Color.*—When opening, upper surface: Near RHS Red 44B, lighter towards the base near Orange 28B, base near Green-Yellow 1C. When opening, lower surface: RHS Red 47C, lighter towards the base near Red 38A, near Yellow-Green 150C at the base. Fully opened, upper surface: Near RHS Red 44C, lighter towards the base, near Orange-Red 33C base near Green-Yellow 1C. Fully opened, lower surface: Outer margin near RHS Red 42B, main surface Orange-Red 35B, base near Yellow-Green 150B.
Spurs: No spurs present.
Sepals: No sepals.
Tepals:
*Quantity.*—Average: 19.
*Length.*—2.1 cm.
*Width.*—2.2 cm.
*Shape (overall).*—Orbicular to broad obovate. Apex: rounded. Base: attenuate.
*Margin.*—Entire.
*Color, both surfaces.*—Near RHS 9A, outer margin near Red 44C.
Peduncles:
*Length.*—5.5 cm.
*Diameter.*—0.5 cm.
*Angle.*—About 25° to the lateral branch.
*Strength.*—Weak.
*Texture.*—Smooth, slightly glossy.
*Color.*—RHS Yellow-Green 146C.
Pedicels:
*Length.*—Average 1.5 cm.
*Diameter.*—Average 0.4 cm.

*Angle.*—About 75°.

*Strength.*—Moderate.

*Texture.*—Smooth, slightly glossy.

*Color.*—RHS Yellow-Green 146A.

Fragrance: No.

REPRODUCTIVE ORGANS

Stamens: No stamens observed.

Anthers: No anthers observed.

Pistil: No pistil observed.

OTHER CHARACTERISTICS

Seeds and fruits: No seeds/fruits observed.

Disease/pest resistance: Neither resistance nor susceptibility to normal pathogens and pests of *Begonia elatior* have been observed.

Temperature tolerance: Indoor plant, no frost tolerance. Observed to tolerate high temperatures to at least 35° C.

What is claimed is:

1. A new and distinct cultivar of *Begonia elatior* plant named 'HV01B1' as herein illustrated and described.

* * * * *